United States Patent [19]

Eckerle et al.

[11] Patent Number: 5,065,765
[45] Date of Patent: Nov. 19, 1991

[54] COMPENSATION FOR TONOMETER SENSOR CROSSTALK AND ELEMENT SPACING

[75] Inventors: Joseph S. Eckerle, Redwood City; Roy Kornbluh, Palo Alto, both of Calif.

[73] Assignee: Colin Electronics Co., Ltd., Japan

[21] Appl. No.: 470,241

[22] Filed: Jan. 25, 1990

Related U.S. Application Data

[63] Continuation-in-part of Ser. No. 370,308, Jun. 23, 1989, abandoned.

[51] Int. Cl.$^5$ .............................................. A61B 5/02
[52] U.S. Cl. .................................... 128/672; 128/901; 128/681
[58] Field of Search ............................... 128/672–675, 128/687–690, 715, 681, 901

[56] References Cited

U.S. PATENT DOCUMENTS

| 4,799,491 | 1/1989 | Eckerle | 128/672 |
| 4,802,488 | 2/1989 | Eckerle | 128/672 |
| 4,830,020 | 5/1989 | Ruth | 128/901 |
| 4,889,133 | 12/1989 | Nelson et al. | 128/681 |
| 4,893,631 | 1/1990 | Wenzel et al. | 128/672 |
| 4,924,871 | 5/1990 | Honeyager | 128/672 |

Primary Examiner—Francis Jaworski
Assistant Examiner—George Manuel
Attorney, Agent, or Firm—Oliff & Berridge

[57] ABSTRACT

A method and apparatus for determining and compensating for the crosstalk behavior and element spacing of an arterial tonometer sensor in order to obtain a more accurate blood pressure measurement. The crosstalk behavior and the effects of element spacing in a tonometer sensor having a plurality of sensing elements located on a single diaphragm is derived using advanced modeling techniques. An error correction factor look-up table is computed and applied to an uncorrected blood pressure measurement, resulting in increased accuracy.

37 Claims, 13 Drawing Sheets

COMPENSATION FOR TONOMETER SENSOR CROSSTALK AND ELEMENT SPACING

BACKGROUND OF THE INVENTION

This is a Continuation-In-Part of patent application Ser. No. 07/370,308 filed June 23, 1989 now abandoned.

The present invention relates generally to a method for increasing the accuracy of an arterial tonometer blood pressure measuring instrument. More specifically, the present invention provides a method to compensate for the known effects of crosstalk and sensing element spacing in an arterial tonometer instrument having a sensor with a plurality of pressure sensing elements, thus providing a more accurate measurement of blood pressure.

Arterial tonometers are used for noninvasively and continuously monitoring the blood pressure of a subject. The arterial tonometer sensor typically is placed over a superficial artery such as the radial artery "pulse point" at the wrist of a human subject. The tonometer sensor is placed against the artery with a sufficient hold down force such that one or several pressure sensing elements comprising the sensor measure the pressure applied locally by the skin adjacent to the artery. The principles of arterial tonometer instruments are described in detail in U.S. Pat. No. 4,802,488 to Eckerle, the disclosure of which is herein incorporated by reference.

Because of various physiological and practical considerations, arterial tonometer sensors are often comprised of a linear array of individual pressure sensing elements which are positioned against the skin orthogonally to a superficial artery (an artery located near the surface of the skin). Ideally, the linear spacing of the sensing elements is such that at least one, although preferably more, is positioned directly above the superficial artery. Measurements of the pressure exerted by the artery (and transmitted through the skin) on each of the sensing elements are taken, and an indication of arterial blood pressure is obtained based on these measurements.

One design of an arterial tonometer sensor comprises a single rectangular diaphragm etched in a silicon substrate with a closely spaced linear array of piezoresistive strain sensing elements deposited in the diaphragm. When a region of the diaphragm is subjected to an applied pressure, a resulting deflection occurs which creates a strain in the strain-sensing elements in proportion to the magnitude of the applied pressure. The array of closely spaced pressure sensing elements has the distinct advantage of providing a more reliable measurement of arterial blood pressure because the more closely the individual elements are placed on the diaphragm, the more likely it is that one or more elements will be located directly above the artery for increased measurement accuracy. It can be said that closely-spaced elements provide better "spatial resolution."

A problem encountered with a plurality of closely spaced elements on a single diaphragm (or multiple diaphragms) is that crosstalk between the elements becomes inevitable. Crosstalk occurs when one region of a diaphragm is subjected to a pressure and, as a result, pressure sensing elements in other regions are affected. Prior arterial tonometers attempted to avoid such crosstalk behavior by physically increasing the spacing among the elements in the tonometer sensor. This, however, was counterproductive to the goal of increased spatial resolution explained above.

Another problem encountered with a plurality of closely spaced elements is that manufacturing limitations restrict how closely the elements may in fact be spaced in relation to one another. The element spacing often ranges from 0.2 mm to 0.4 mm. Thus, while ideally at least one element is spaced directly above the center of the artery, it is often the case that the nearest element to the center of the artery is offset by as much as one-half of the element spacing.

Thus, there remains a need for a method and system for compensating for such crosstalk and element spacing so as to retain the benefit of increased spatial resolution afforded by a plurality of closely spaced sensing elements In addition, there remains a need for determining the magnitude of such crosstalk of a tonometer sensor so that the crosstalk behavior may be properly compensated.

SUMMARY OF THE INVENTION

Accordingly, the present invention has been developed to overcome the foregoing shortcomings of existing tonometer sensors.

It is therefore an object of the present invention to provide a method and apparatus for compensating for predetermined crosstalk and element spacing in an arterial tonometer sensor having a plurality of pressure sensing elements disposed on a single diaphragm, in order to provide improved accuracy in the measurement of intra-arterial pressure.

Thus, in accordance with one embodiment of the present invention a method is provided for compensating for crosstalk behavior and element spacing of an arterial tonometer having a plurality of pressure sensing elements on a single diaphragm, the method comprising the steps of determining a measured artery pressure profile of a subject artery, using at least one characteristic of the measured artery pressure profile to determine an error correction factor, determining an uncorrected blood pressure value, and calculating a corrected blood pressure value by applying the error correction factor to the uncorrected blood pressure value.

In accordance with another embodiment of the present invention, a method is provided for constructing an error correction factor look-up table for use in compensating for crosstalk and element spacing of the sensor of an arterial tonometer instrument, which sensor has a plurality of sensing elements disposed on at least one diaphragm, the method including the steps of modeling said diaphragm, using the results of said modeling to obtain responses of the diaphragm to artery pressure profiles typical of those measured by a tonometer sensor placed over a superficial artery, using the diaphragm responses to estimate errors in blood pressure measurements for the typical artery pressure profiles, and calculating error correction factors necessary to compensate for these errors.

In accordance with yet another embodiment of the present invention, an apparatus for externally measuring blood pressure in an artery is provided, the apparatus including an arterial tonometer instrument, including a sensor having a plurality of pressure sensing elements disposed on at least one diaphragm, for determining an uncorrected blood pressure value, and a device for determining an apparent artery width of the artery, determining a dip depth for the artery, utilizing the apparent artery width and dip depth to determine an error correction factor, and for calculating a corrected blood pressure value by applying the error correction factor to the uncorrected blood pressure value.

These and other aspects and advantages of the present invention are described in or are apparent from the following detailed description of the preferred embodiments.

BRIEF DESCRIPTION OF THE DRAWINGS

The preferred embodiments are described with reference to the drawings in which.

DESCRIPTION OF THE PREFERRED EMBODIMENTS

Figure 1:
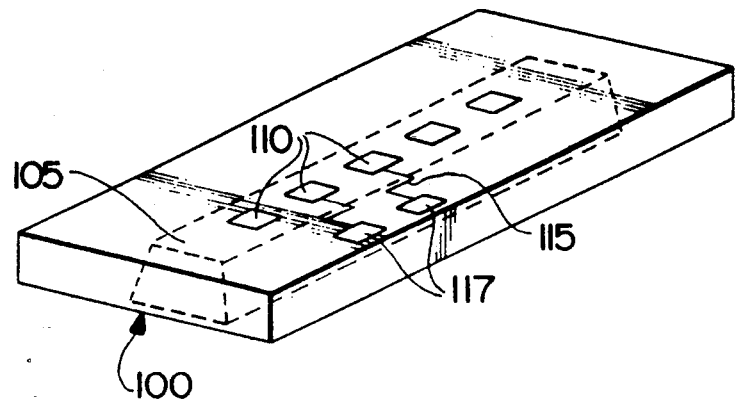
FIG. 1 is a perspective view of a tonometer sensor illustrating a plurality of pressure sensing elements positioned on a thin diaphragm.

Referring to FIG. 1, an arterial tonometer sensor 100 is shown having a single diaphragm 105 and a plurality of closely spaced pressure sensing elements 110. Each individual sensing element 110 is connected via conductors 115 and bonding pads 117 to measurement means (not shown) included in the tonometer instrument.

Figure 2:
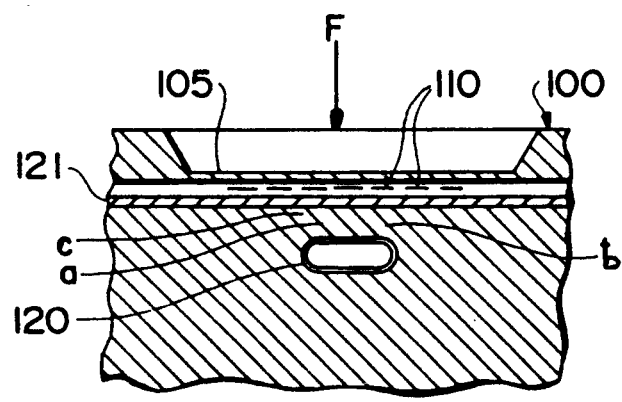
FIG. 2 is a cross-sectional view of an arterial tonometer sensor diaphragm with pressure sensing elements pressed against a partially flattened radial artery located in a subject's wrist.

FIG. 2 is a cross-sectional view of the sensor 100 being held against artery 120 with sufficient hold down force F such that compressed artery 120 exerts, via the skin 121, pressure against individual sensing elements 110. This pressure, as applied against each element 110 in diaphragm 105, is non-uniform and depends upon the location of each element in relation to the artery. Also, because elements 110 are closely spaced, a pressure exerted against the sensor by the artery 120 (through the skin) in the region a is also likely to create a pressure or stress effect on adjacent regions of the diaphragm 105, such as, for example, in the vicinity of regions b and c. This effect will be referred to hereinafter as "crosstalk".

Crosstalk in the tonometer sensor reduces the accuracy of the blood pressure measurement by preventing the tonometer sensor from accurately mapping the pressure profile of the artery. According to the teachings of U.S. Pat. No. 4,802,488, blood pressure may be measured using an artery pressure by noting the sensed pressure at roughly the mid-point of the artery which corresponds to a spatial local minimum in the pressure profile across the width of the artery. While the apparent width of an artery varies with the individual, it will span several elements of the tonometer sensor if the element spacing is small enough. (This is the ideal case. If the subject is particularly small, the artery may only span one or two elements. In these cases, the corrections described here are not applicable.) It is therefore necessary that the sensor elements map the pressure profile of the artery to, at the very least, identify and provide an accurate measurement at the spatial local minimum. If crosstalk between the sensor elements is too great, then accurate blood pressure measurement will not be possible because the differing pressures across the width of the artery will have a cumulative effect on the pressure measured by any element on the diaphragm.

Figure 3:
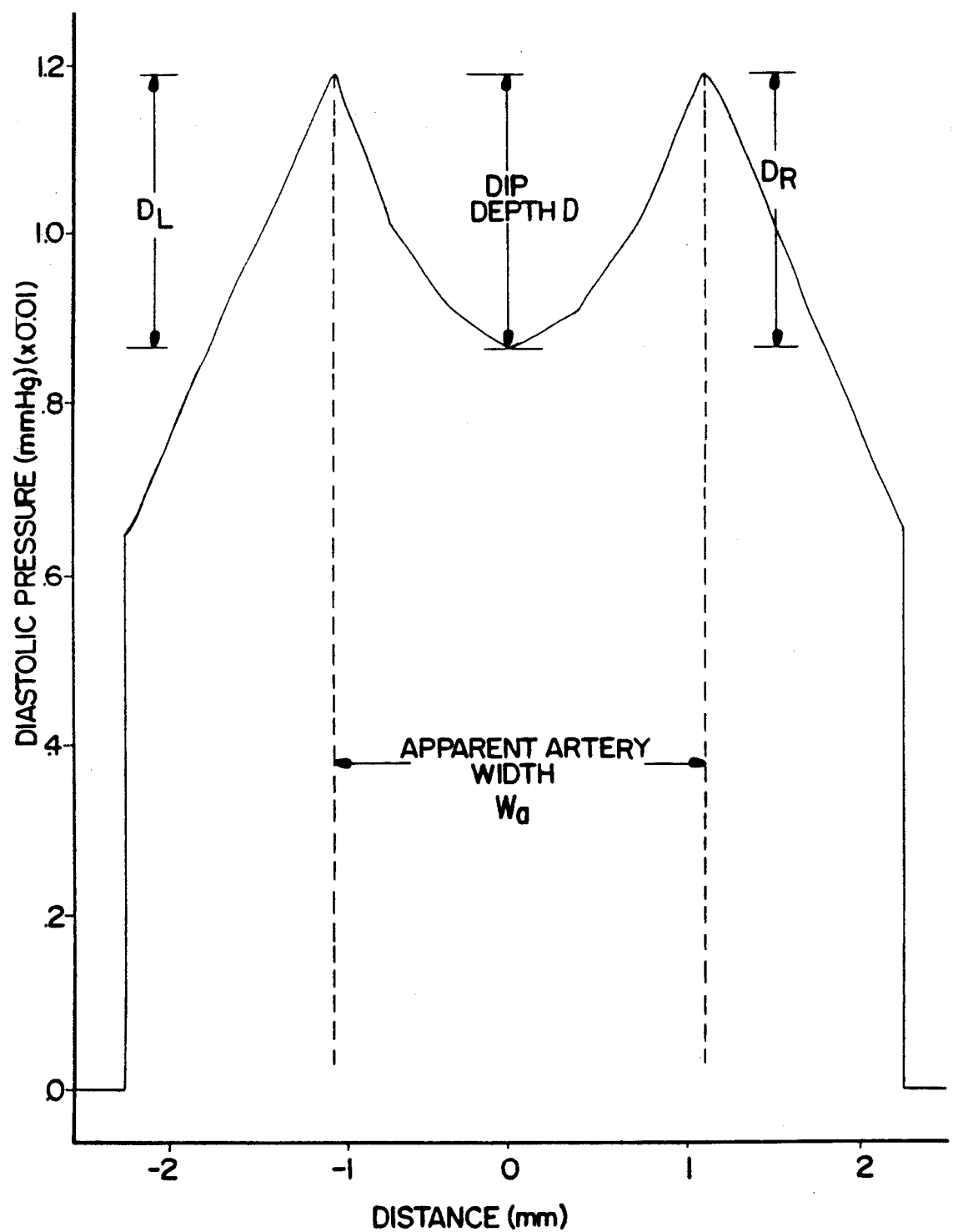
FIG. 3 shows a plot of diastolic pressure versus distance.

FIG. 3 shows a typical arterial pressure profile. FIG. 3 is based on the measurement of the radial artery of an 80Kg male made by an eight element tonometer sensor. (See J. S. Eckerle, J. Fredrick and P. Jeuck, "Toward a Practical Tonometric Blood Pressure Instrument," Proc. 6th Annu. Conf. IEEE/Eng. Med. Biol. Soc., pp. 635–641 (1984)). The information from the eight sensor elements was interpolated and extrapolated to yield an arterial pressure profile that is symmetric about the center of the artery and assumed to be zero beyond the edges of the artery. FIG. 3 shows this stereotypical pressure profile and the important characteristic parameters of dip depth and apparent artery width, $W_a$. This particular pressure profile, with an apparent artery width of 2.25 mm, will be termed the "baseline" pressure profile for purposes of this disclosure. Variations in the apparent artery width would correspond directly to variations in the width of the artery as might be found in large and small people. The apparent artery width differs from the artery diameter because the artery is compressed by the sensor when the FIG. 3 profile is obtained. A convenient estimate is that the artery diameter is about 0.9 times the apparent artery width.

Figure 4:
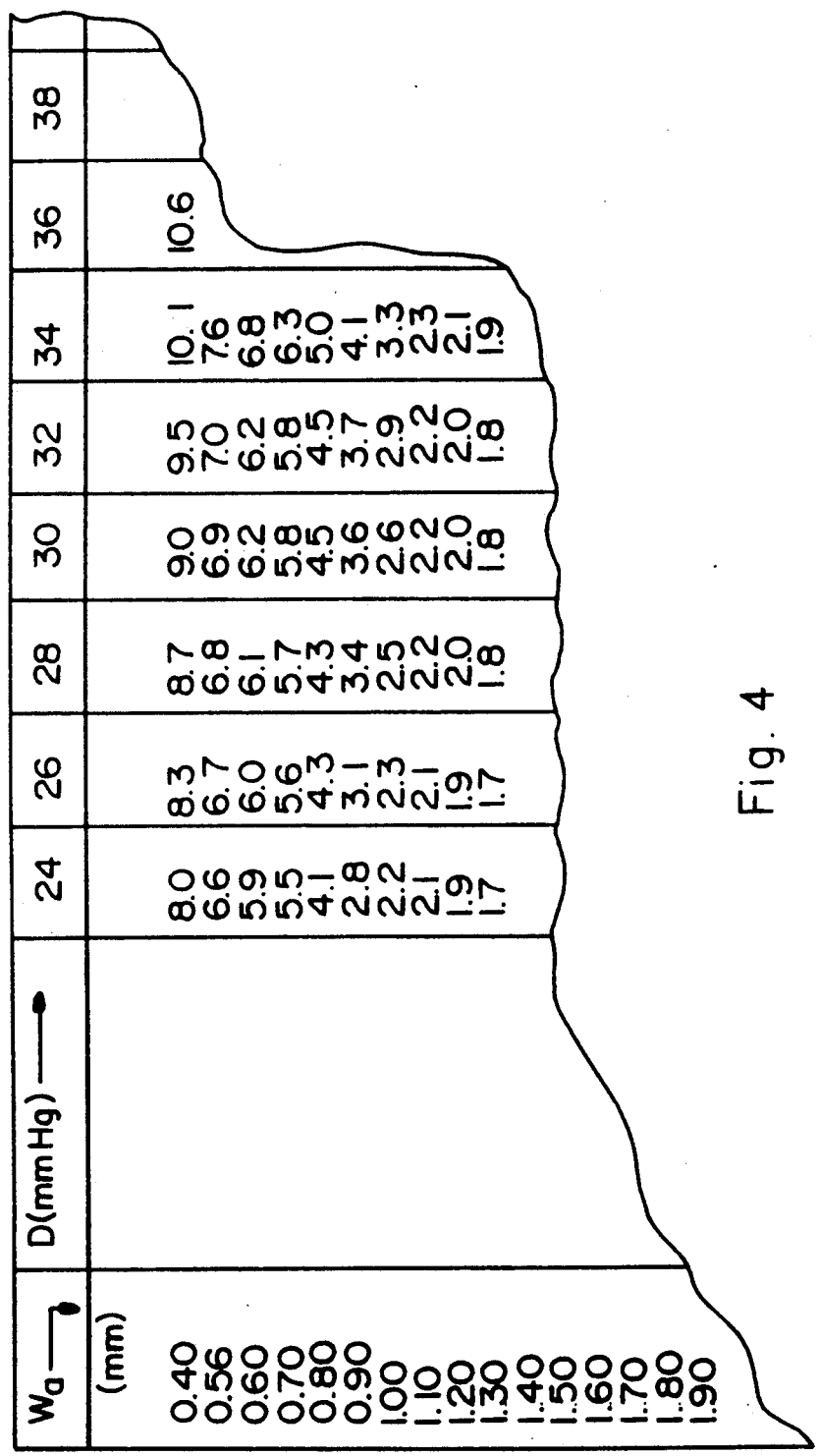
FIG. 4 shows part of a crosstalk error correction lookup table containing several crosstalk error correction factor entries in accordance with the present invention.

The present invention compensates for the crosstalk behavior of a tonometer sensor. By using a precomputed crosstalk error correction factor look-up table and applying an appropriate crosstalk error correction factor to an uncorrected blood pressure measurement, the invention provides a blood pressure measurement of increased accuracy. More specifically, the plurality of sensing elements map the measured arterial pressure profile of the subject artery. Identifying characteristics of the measured pressure profile are then determined and utilized to reference a similarly characterized entry in the predetermined crosstalk error correction factor look-up table. The uncorrected systolic or diastolic blood pressure value determined by the tonometer instrument is then corrected by applying the appropriate crosstalk error correction factor. FIG. 4 shows part of a precomputed error correction factor look-up table.

In the preferred embodiment, the specific characteristic parameters that identify the measured artery pressure profile are apparent artery width $W_a$ and dip depth D. (See FIG. 3.) A crosstalk error look-up table is indexed according to these parameters.

The amount of crosstalk which occurs in the tonometer sensor 100 is affected by the geometry of the diaphragm 105, and the shape of the applied artery pressure profile. (See FIG. 3.) Methods detailed below are used to compute the amount of crosstalk that occurs in order to construct the crosstalk error correction factor look-up table, used for compensating for the error caused by crosstalk. One such method includes analytically modeling the sensor diaphragm and determining its responses to applied pressure profiles typical of those measured by a tonometer sensor. Another method consists of using finite element modeling (FEM) techniques to similarly determine the responses of the sensor diaphragm.

Figure 5A:
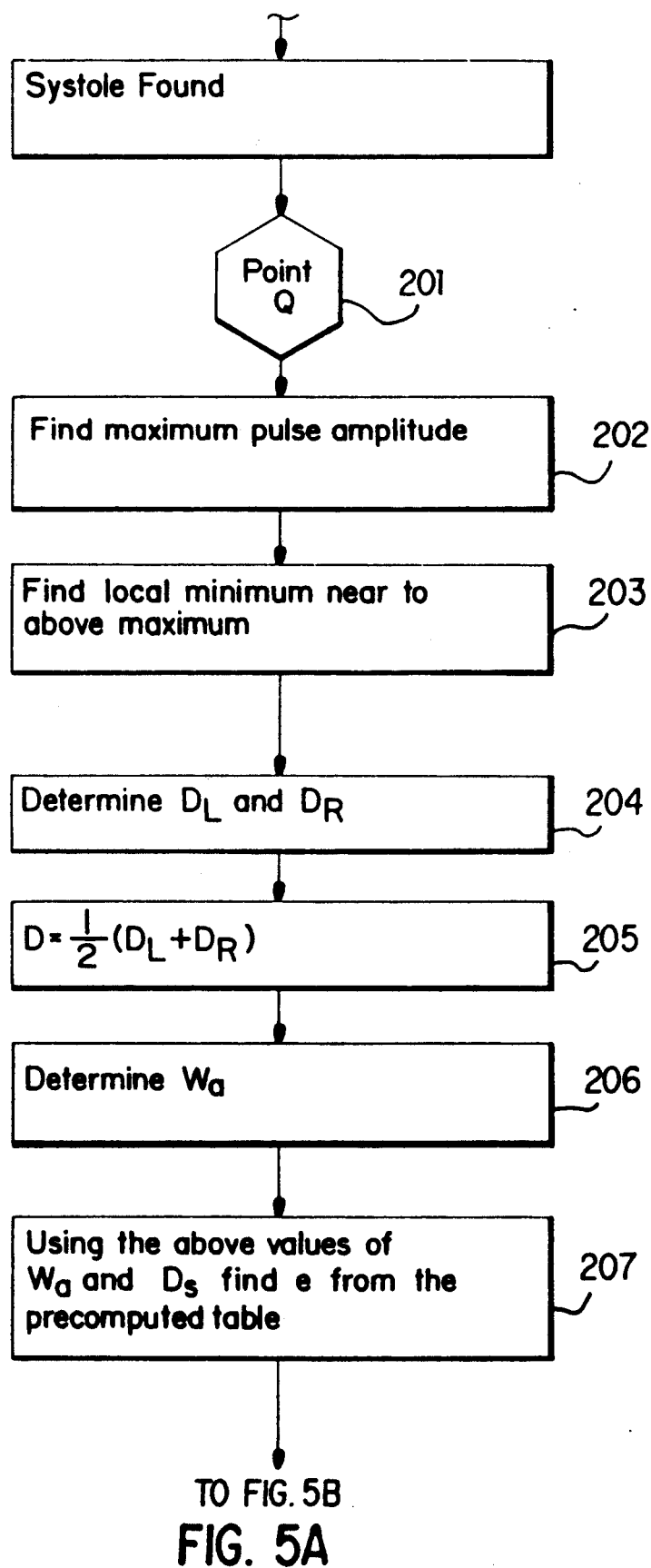
FIGS. 5A and B are a flowchart describing an arterial tonometer measurement and the crosstalk and element spacing error compensation process in accordance with the present invention.

The detailed operation of the invention can be understood by reference to the flow chart of FIGS. 5A and B. In the preferred embodiment of the present invention, the operations shown in this figure are incorporated in the control computer of the tonometer instrument. The instrument user would normally be unaware of these operations. Most tonometer instrument algorithms wait until a heartbeat has occurred (indicated by a systole on the the blood pressure waveform) before determining the artery location relative to the various elements of the tonometer sensor, and blood pressures (systolic and diastolic) for that heartbeat. For the purposes of this disclosure, that point in the instrument algorithm will be called Point Q.

Referring to FIG. 5A, after reaching Point Q at step 201, the instrument determines the location of the maximum pulse amplitude (difference between systolic and diastolic pressures) at step 202. Next, at step 203 it determines the location of the spatial local minimum in the measured pressure near to the maximum pulse amplitude. Next, the instrument estimates the "dip depth." (See FIG. 3.) Dip depth will not generally be the same for the two sides of an artery. Therefore, a left and right dip depth, $D_L$ and $D_R$ respectively as shown in FIG. 3, are computed In order to compute $D_L$ and $D_R$, the instrument in step 204 must first determine the locations of the left and right edges of the artery. (See FIG. 3.) If there is a peak (i.e. a local maximum) in the pressure distribution located a reasonable distance (about 0.4 mm to 1.5 mm for adult radial arteries) from the above spatial local minimum, then this peak is assumed to coincide with the edge of the artery. If (unlike the FIG. 3 profile) there is no peak at a reasonable distance from the minimum, then the location where the pulse amplitude reaches a fixed fraction (typically, about 60% to 90%) of its maximum value is taken as the location of the edge of the artery 120. Once the artery edges have been found, $D_L$ (or $D_R$) is simply the difference between the measured diastolic pressure at the left (or right) edge and the diastolic pressure at the local minimum.

Referring again to FIG. 5A, the dip depth, D, is found at step 205 by taking the average of $D_L$ and $D_R$. Next, at step 206 the apparent artery width, $W_a$, is found. This is simply the distance between the left and right edges of the artery 120 described above.

The values of $W_a$ and D are then used at step 207 to find the appropriate entry, e, in the crosstalk error correction factor look-up table corresponding to the parameters of the subject.

Figure 5B:
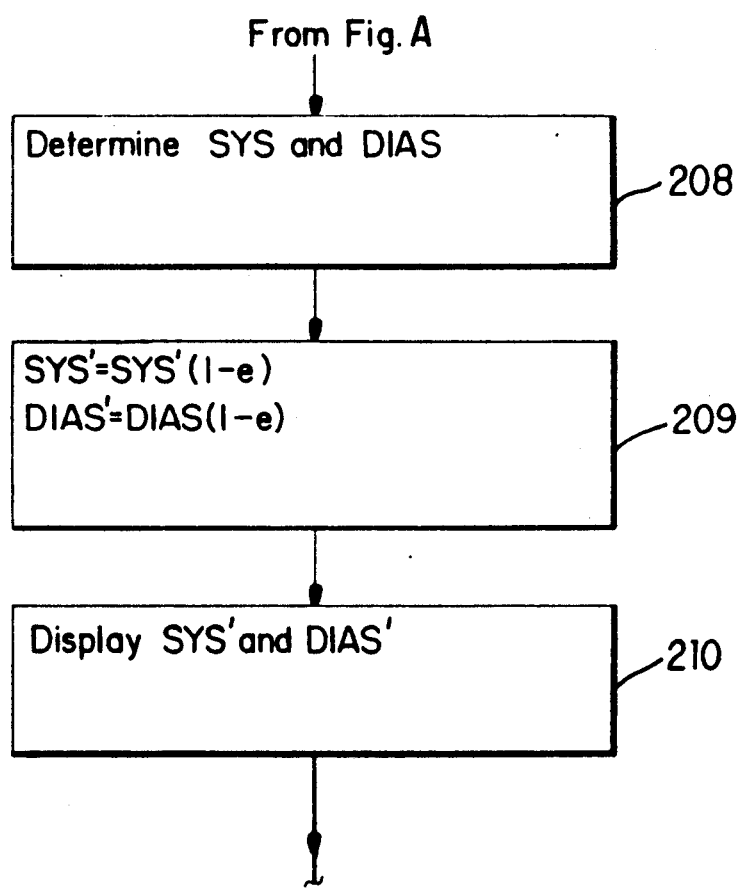

Referring now to FIG. 5B, the systolic and diastolic blood pressures for the current heartbeat are found at step 208 by traditional methods. These are denoted by SYS and DIAS, respectively. Next, these values are corrected at step 209 by applying the correction factor, e, as shown. The corrected values, SYS' and DIAS', are then displayed at step 210.

Some tonometer instruments display the entire blood-pressure waveform in addition to systolic and diastolic pressures. In these instruments, each successive pressure sample (typically 30 to 400 samples per second are displayed) may be corrected by applying the correction factor, e, before it is displayed.

As indicated above, modeling techniques are used to compute the amount of crosstalk which occurs in the tonometer sensor so that a crosstalk error correction factor look-up table (FIG. 4) may be constructed. From this table, crosstalk error correction factor values (e) may be obtained. In one embodiment an analytical model of the tonometer sensor geometry may be employed to determine the degree of crosstalk. In another embodiment, finite element modeling techniques may be employed.

Figure 6A:
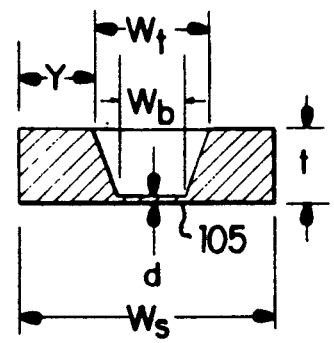
FIGS. 6A, B and C are perspective and cross-sectional views of the baseline geometry of a tonometer sensor of the type considered in the present invention.

An assumed geometry for the tonometer sensor 100 is shown in FIGS. 6A and B. Because the model is linear with respect to the applied load, the teachings of this invention can be applied to geometrically similar sensors by using appropriate scaling. For the calculations described below, $W_b$ is equal to 0.25 mm. This geometry will be called the "baseline" sensor geometry.

Figure 6B:
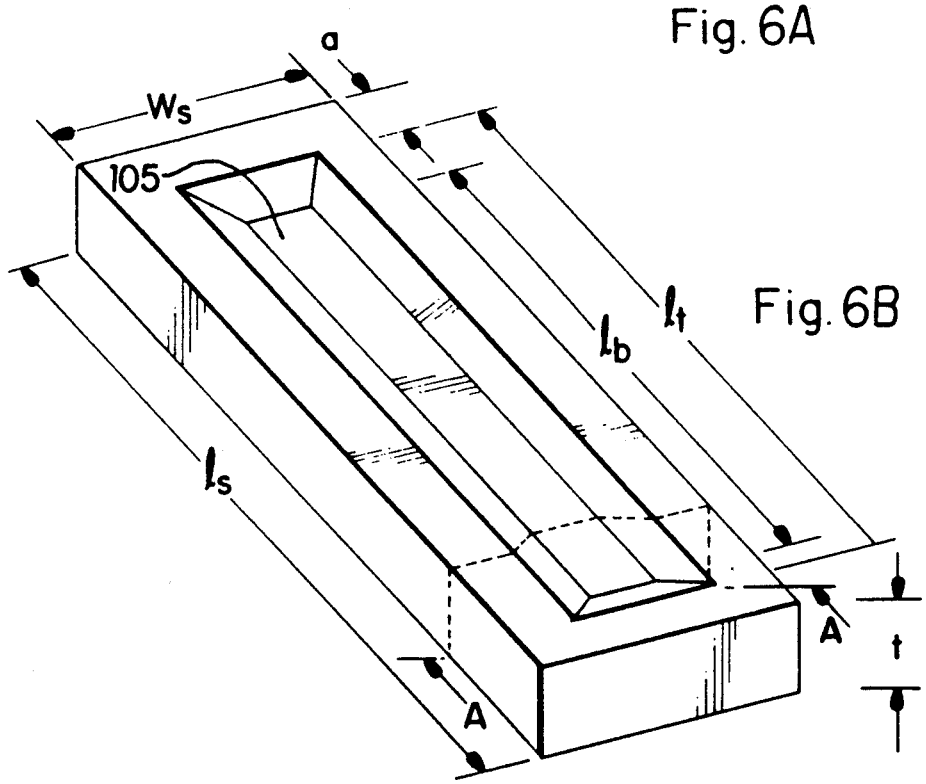

Using analytical modeling techniques, an exact analytical solution for the diaphragm pressure response that includes the full geometry of the sensor 100 is not feasible. Instead the diaphragm 105 alone may be analytically modeled as a plate, rigidly-clamped at its four edges. The accuracy of the results using these assumed boundary conditions may be evaluated by using a finite element model that more accurately models the sloping walls of the silicon structure around the periphery of the diaphragm 105 shown in FIGS. 6A and 6B. An additional simplification is that the modulus of elasticity of the silicon is assumed to be isotropic. This assumption is appropriate since the uncertainty of the modulus in any direction, based upon the range of values found in the literature, is greater than the variation between directions. The value of $1.88 \times 10^{11}$ Pa used is that most commonly found in the literature.

Figure 7:
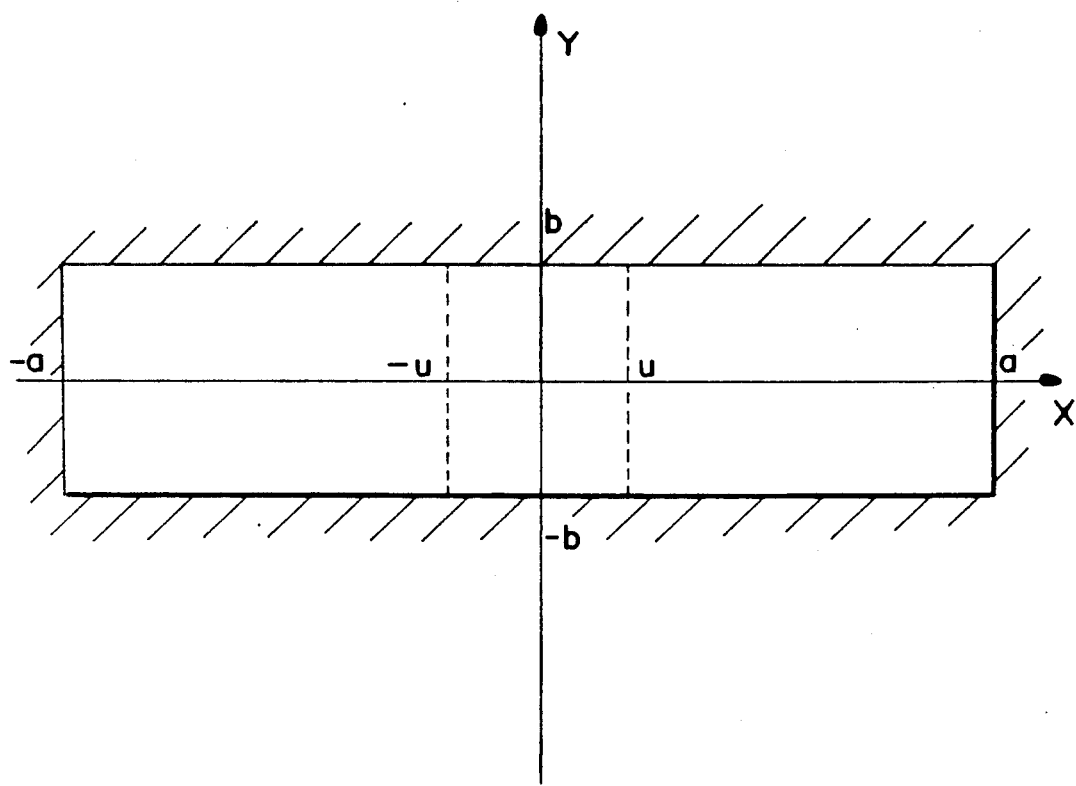
FIG. 7 is a plan view of the parameters used in the analytical model of a diaphragm subject to an applied pressure strip in accordance with the present invention.

The analytical model for the diaphragm 105 is depicted in FIG. 7. A clamped rectangular plate $2a$ long and $2b$ wide is subjected to a strip of pressure P that is $2u$ wide and located symmetrically about the y-axis centerline of the plate. Since this model is linear with respect to the applied pressure, super position may be used to develop the solution to any desired pressure profile that varies only in the x direction. This is accomplished by adding together the solutions for several pressure strips of appropriate widths and magnitudes so that the desired pressure profile is approximated. Further, it will be shown below that the effects of a pressure strip diminish rapidly beyond its edges, so that the requirement that the applied pressure load be located in the center of the diaphragm is not necessary as long as the load is relatively far from the ends ($x = \pm a$) of the diaphragm and the diaphragm is much longer than it is wide. Thus, the symmetric case of FIG. 7 may be used to solve for a wide variety of pressure loadings including those typical of artery pressure profiles.

Published analytical solutions for the response of a clamped plate consider only the relatively simple case of a uniform pressure applied over the entire surface. However, the present invention extends the method developed by Timoshenko (S. Timoshenko and S. Woinowsky-Krieger, "Theory of Plates and Shells," McGraw-Hill Book Co., Inc., New York, 1959) to include the strip loading case of interest.

The analytical solution for the modeled diaphragm is obtained by first using a well known Navier solution to solve for the case of the simply supported plate. Superimposing the solution for a plate subjected to moments distributed along the edges that are chosen to satisfy the clamped-edge boundary conditions, the solution for the deflection may be written as $$w = w_{ss} + w_{clx} + w_{cly}$$

where $w_{ss}$ is the simply-supported deflection and $w_{clx}$ and $w_{cly}$ are the terms for the distributed moments used to satisfy the clamped-edge boundary conditions.

The applied load $$q = \begin{cases} 0 & -a < x < -u \\ P & -u \leq x \leq u \\ 0 & u < x < a \end{cases}$$

is represented by the Fourier series:

$$q(x,y) = \sum_{i=0}^{\infty} \sum_{j=0}^{\infty} q_{ij} \cos\left(\frac{x}{a_i}\right) \cos\left(\frac{y}{b_j}\right)$$

with $$a_i = \frac{2a}{(2i+1)\pi}$$

$$b_j = \frac{2b}{(2j+1)\pi}$$

and $q_{ij} = \frac{4P}{ab} a_i b_j (-1)^j \sin\left(\frac{u}{a_i}\right)$.

Solving the differential equation for the diaphragm deflection, $$\nabla^4 w = \frac{q}{D}$$

the solution is represented by:

$$w_{ss} = \frac{1}{D} \sum_{i=0}^{\infty} \sum_{j=0}^{\infty} q_{ij} \left(\frac{1}{a_i^2} + \frac{1}{b_j^2}\right)^{-2} \cos\left(\frac{x}{a_i}\right) \cos\left(\frac{y}{b_j}\right).$$

The expressions for $w_{clx}$ and $w_{cly}$ are found to be:

$$w_{clx} = \sum_{i=0}^{\infty} \frac{a_i^2 E_i \cos\left(\frac{x}{a_i}\right)}{2D \cosh\left(\frac{b}{a_i}\right)} \left[\frac{b}{a_i} \tanh\left(\frac{b}{a_i}\right) \cosh\left(\frac{y}{a_i}\right) - \frac{y}{a_i} \sinh\left(\frac{y}{a_i}\right)\right]$$

and $$w_{cly} = \sum_{j=0}^{\infty} \frac{b_j^2 F_j \cos\left(\frac{y}{b_j}\right)}{2D \cosh\left(\frac{a}{b_j}\right)} \left[\frac{a}{b_j} \tanh\left(\frac{a}{b_j}\right) \cosh\left(\frac{x}{b_j}\right) - \frac{x}{b_j} \sinh\left(\frac{x}{b_j}\right)\right].$$

Here, E and F are solutions of $$E_i \left[\frac{b}{\cosh^2\left(\frac{b}{a_i}\right)} + a_i \tanh\left(\frac{b}{a_i}\right)\right] +$$

$$\frac{4a_i^3}{a} (-1)^i \sum_{j=0}^{\infty} F_j \frac{(-1)^j}{b_j\left(1 + \frac{a_i^2}{b_j^2}\right)^2} =$$

$$\frac{8Pa_i \sin\left(\frac{u}{a_i}\right)}{ab} \sum_{j=0}^{\infty} \left(\frac{1}{a_i^2} + \frac{1}{b_j^2}\right)^{-2}$$

and $$F_j \left[\frac{a}{\cosh^2\left(\frac{a}{b_j}\right)} + b_j \tanh\left(\frac{a}{b_j}\right)\right] +$$

$$\frac{4b_j^3}{b} (-1)^j \sum_{i=0}^{\infty} E_i \frac{(-1)^i}{a_i\left(1 + \frac{b_j^2}{a_i^2}\right)^2} =$$

$$\frac{8P(-1)^j b_j}{ab} \sum_{j=0}^{\infty} (-1)^i \frac{\sin\left(\frac{u}{a_i}\right)}{\left(\frac{1}{a_i^2} + \frac{1}{b_j^2}\right)^2}.$$

Figure 8:
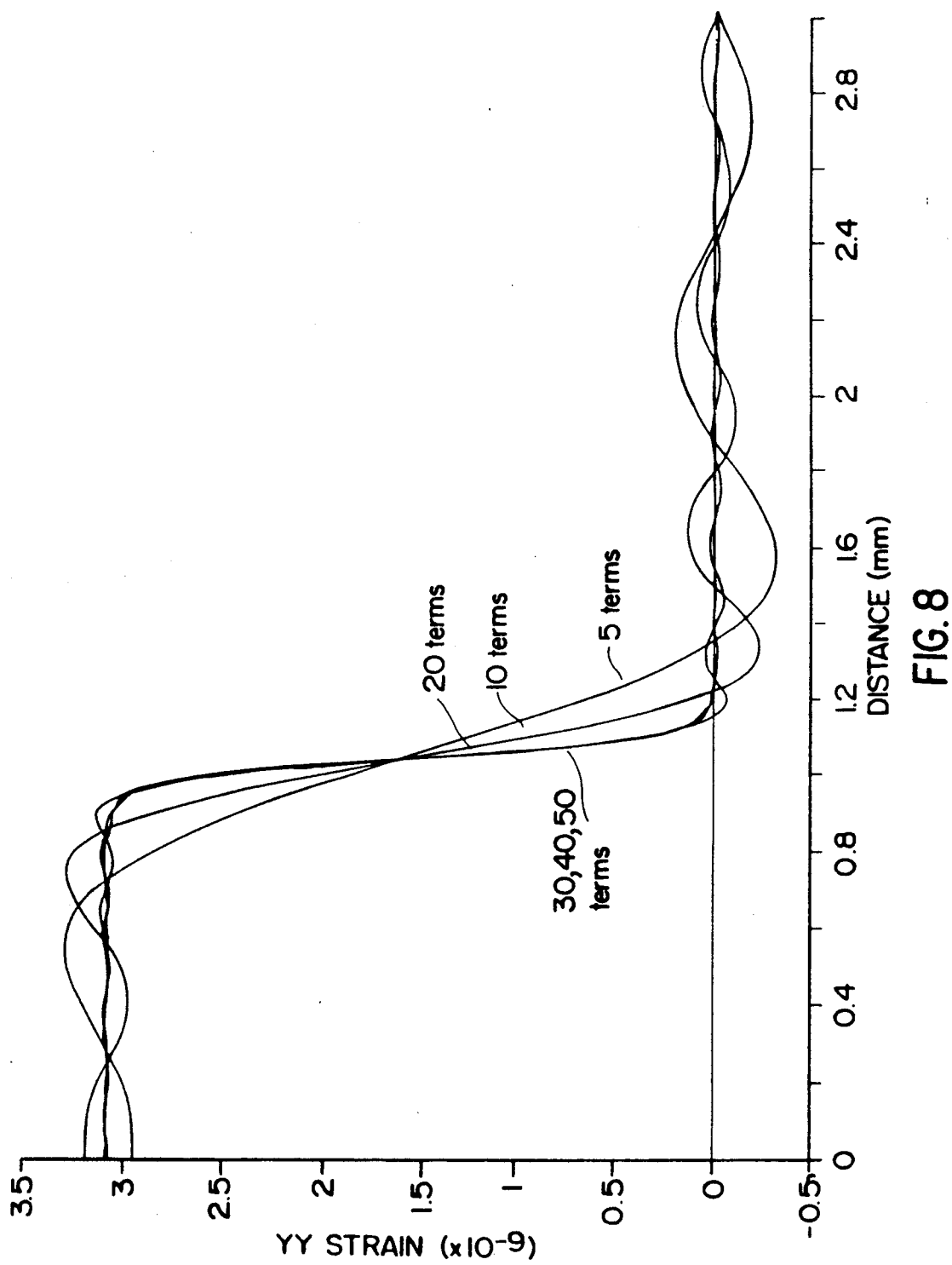
FIG. 8 shows plots of strain response versus distance of a rectangular diaphragm analytical model subjected to a pressure strip in accordance with the present invention.

Since the solution must be approximated with a finite number of terms in a double summation, it is desirable to verify that the solution does indeed converge if a reasonable number of terms are used. FIG. 8 shows the response of a diaphragm with the above-described baseline geometry to a 2mm wide pressure strip as computed using the above analytical expressions. Since the response is symmetric, only half of the response is shown. The distance plotted on the abscissa is the distance from the center of the load. The Y direction strain was chosen for consideration as this will be proportional to the output of sensing elements 110. The results of using 5, 10, 20, 30, 40 and 50 terms for each of the above summations are shown in FIG. 8. The strain shown is measured at the edge of the diaphragm where one would expect to locate strain gages which act as the individual sensing elements 110. When less than twenty terms are used, the oscillatory behavior of the solution composed of sine and cosine terms is clearly evident. As more terms are added, it is clear that the solution does converge to a single curve. Based on this information, at least forty terms for each summation are preferred, and were used, for all analyses described below.

Figure 9:
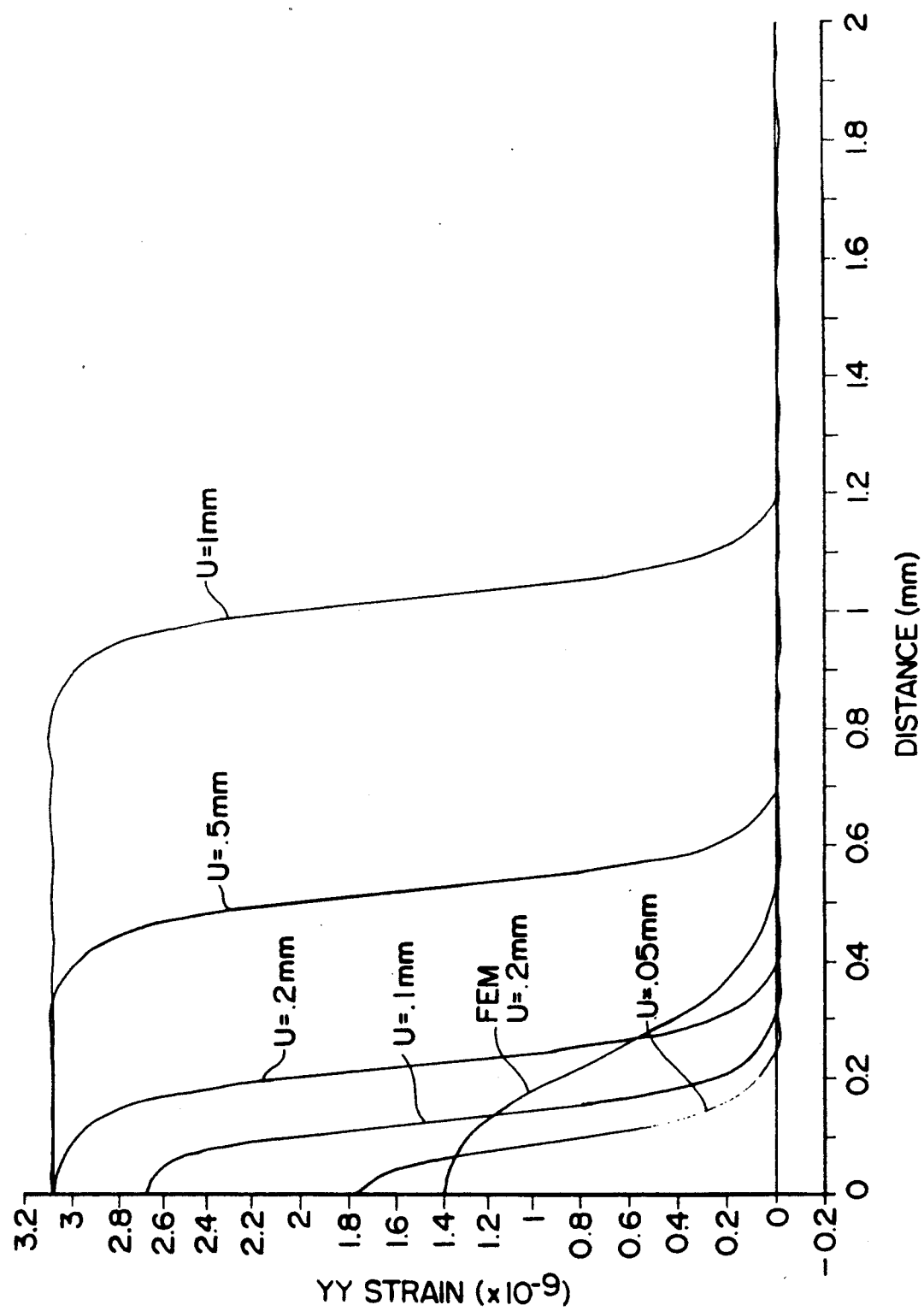
FIG. 9 shows plots of strain response versus distance of a rectangular diaphragm analytical model and finite element model subjected to various widths of applied pressure.

FIG. 9 shows the response of the diaphragm with the above-described baseline geometry to a unit pressure load over a strip 2u in width for several values of u. These results were computed with the analytical model described above.

The FIG. 9 results indicate that the magnitude of the response to more rapidly changing pressures in the X direction, i.e. narrower strips, will be diminished. Further, regardless of the width of the pressure strip, the response diminishes at the same rate beyond the edge of the strip. This effect can better be seen in FIG. 10 which shows the response of the diaphragm (denoted "analytical") beyond the edge of the applied pressure strip. The response is identical for all of the pressure strip widths. The normalized YY strain shown on the ordinate is the strain divided by the maximum strain. While these results are for a pressure load at the center of the diaphragm, the shape of the response will be very similar at any location along the diaphragm. An exception is at the ends of the diaphragm where the magnitude of the response is diminished and the shape may differ as well.

Figure 10:
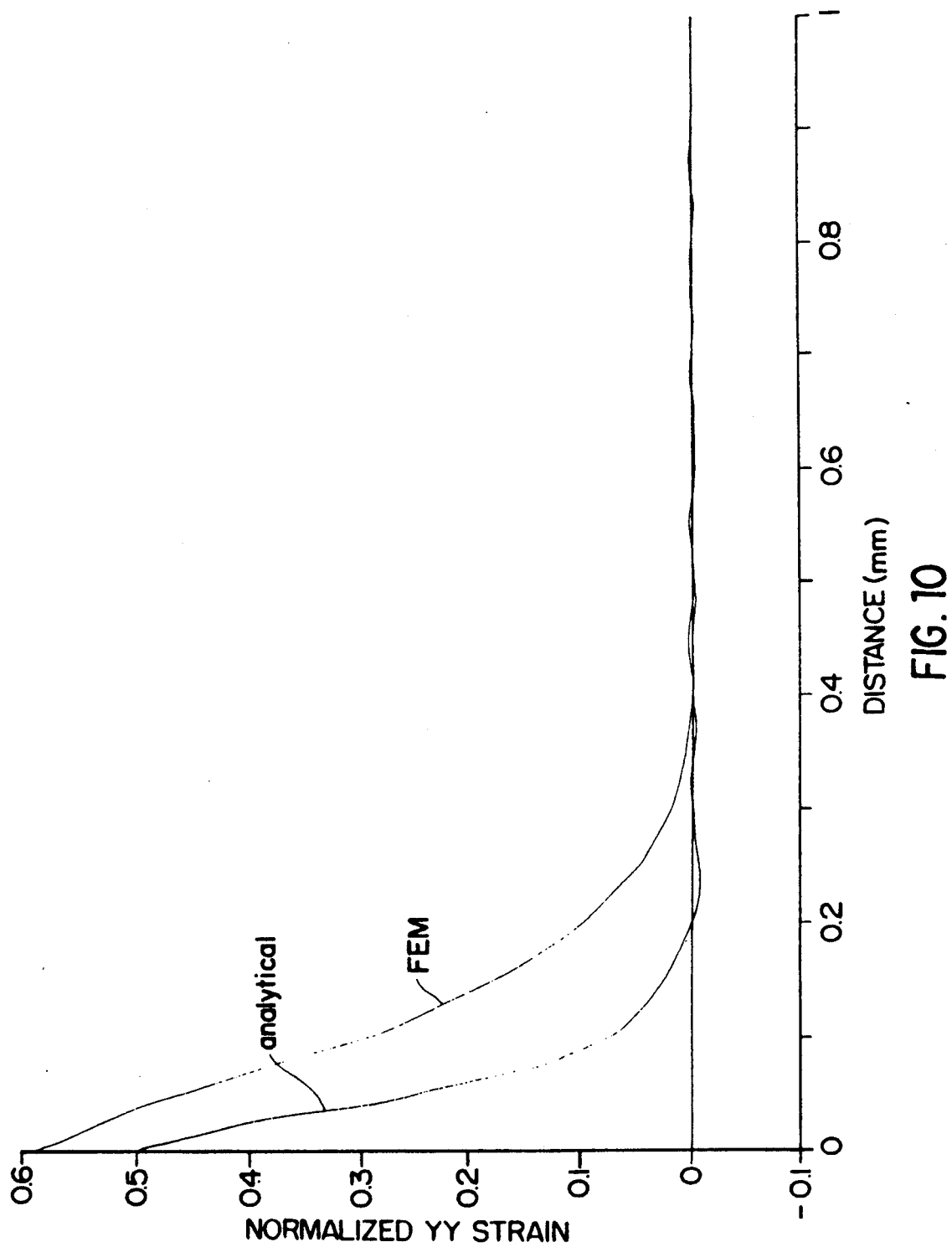
FIG. 10 shows plots of the normalized strain response versus distance extending beyond the edge of an applied pressure strip in accordance with the analytical and finite element models of the present invention.

The analytical results shown in FIG. 10 indicate that the amount of strain measured beyond the edges of the applied load, the crosstalk, falls below 5% at roughly 0.12 mm from the edge.

Using the analytical model, the response of the diaphragm to a typical artery pressure profile (See FIG. 3.) and the effect of artery width on the accuracy of the response was determined. Superposition was used as described above to obtain the response to an artery pressure profile that varies in the X-direction.

Figure 11:
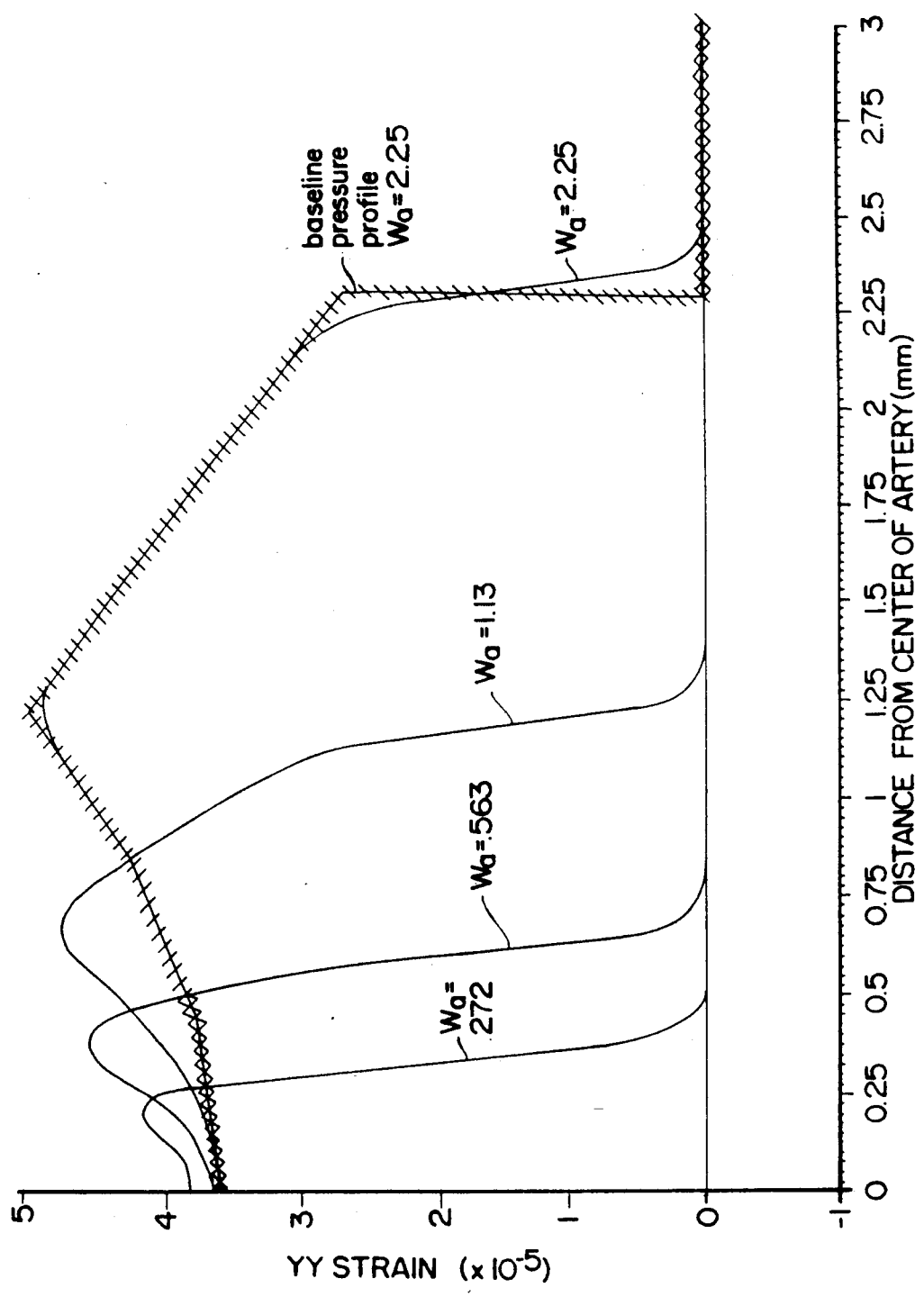
FIG. 11 shows plots of strain response versus distance for the analytically modeled diaphragm response for several apparent artery widths in accordance with the present invention.

FIG. 11 shows the strain response of the diaphragm to several different apparent artery widths. The artery pressure profile shown in this figure has been scaled (normalized) to match the strain response by assuming that the strain response was calibrated to the applied pressure by applying a known, uniform pressure to the diaphragm. Using this technique, a strain of $3.08 \times 10^{-9}$ would correspond to a pressure of 1 Pa (according to the analytical model).

The magnitude of each of the applied pressure profiles used in constructing FIG. 11 was the same regardless of the apparent artery width. FIG. 11 shows that for the baseline artery pressure profile ($W_a=2.25$), there is close agreement between the normalized artery pressure profile and the resulting strain response. However, for narrower arteries, the dip depth in the response decreases and the deviation in the strain value (from the ideal value) at the minimum of the dip becomes greater. These results are consistent with the above analysis using pressure strip loads which showed that the diaphragm would accurately reflect the applied pressure as long as the pressure did not change rapidly with distance. The narrower the artery, the faster the pressure changes with distance.

Figure 12:
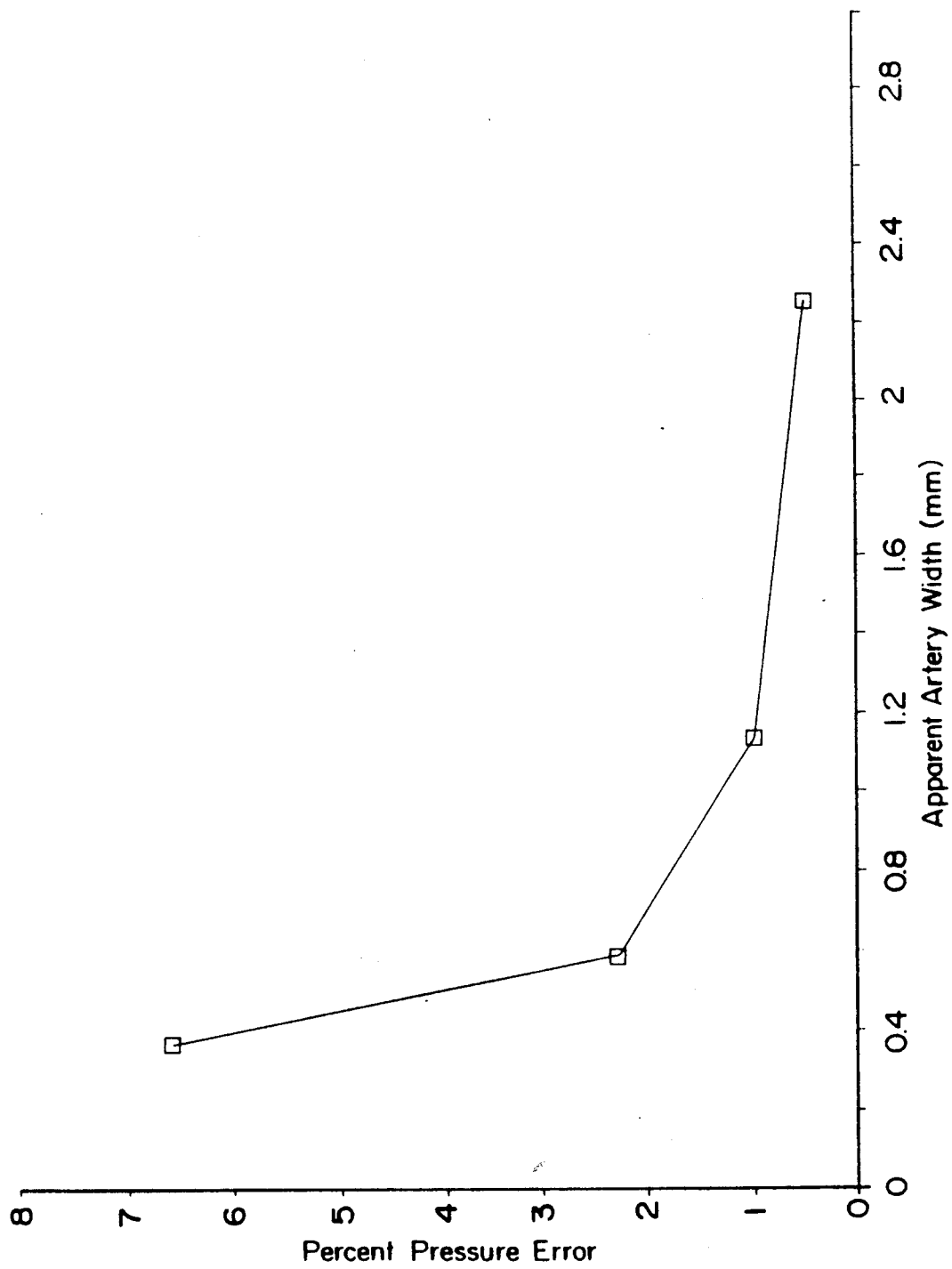
FIG. 12 shows a plot of percent pressure error in diastolic pressure measurement versus apparent artery width in accordance with the analytical model of the present invention.

According to the traditional principles of tonometry, the measured strain at the minimum of the dip in the strain response is taken to be proportional to the arterial blood pressure. (See, for example, U.S. Pat. No. 4,802,488.) Thus, for accurate measurement of blood pressure, this strain value measured at the minimum must accurately reflect the true pressure applied to the sensor. The influence of artery size on this measured strain as determined in FIG. 11 is shown in FIG. 12. In this figure, the percent pressure error is the difference between the measured strain response and ideal strain response to the arterial pressure profile at the minimum of the dip divided by the ideal value. The percent pressure error remains fairly low (less than 3%) for apparent artery widths as small as one fourth of the baseline width (0.56 mm). However, clearly the response is more accurate for wider arteries. The percent pressure errors of FIG. 12 may then be used to establish the crosstalk error correction factor values (e) as shown in FIG. 4.

Note, however, that the above analysis assumes that the strain in the sensor diaphragm is measured precisely at the minimum of the dip. This situation, of course, is not always true since the strain can only be measured by gages spaced at finite intervals along the diaphragm. Thus, the strain measurement could be made at as much as one half of the spacing interval from the minimum of the dip, further contributing to inaccuracies in blood pressure measurement.

Figure 13:
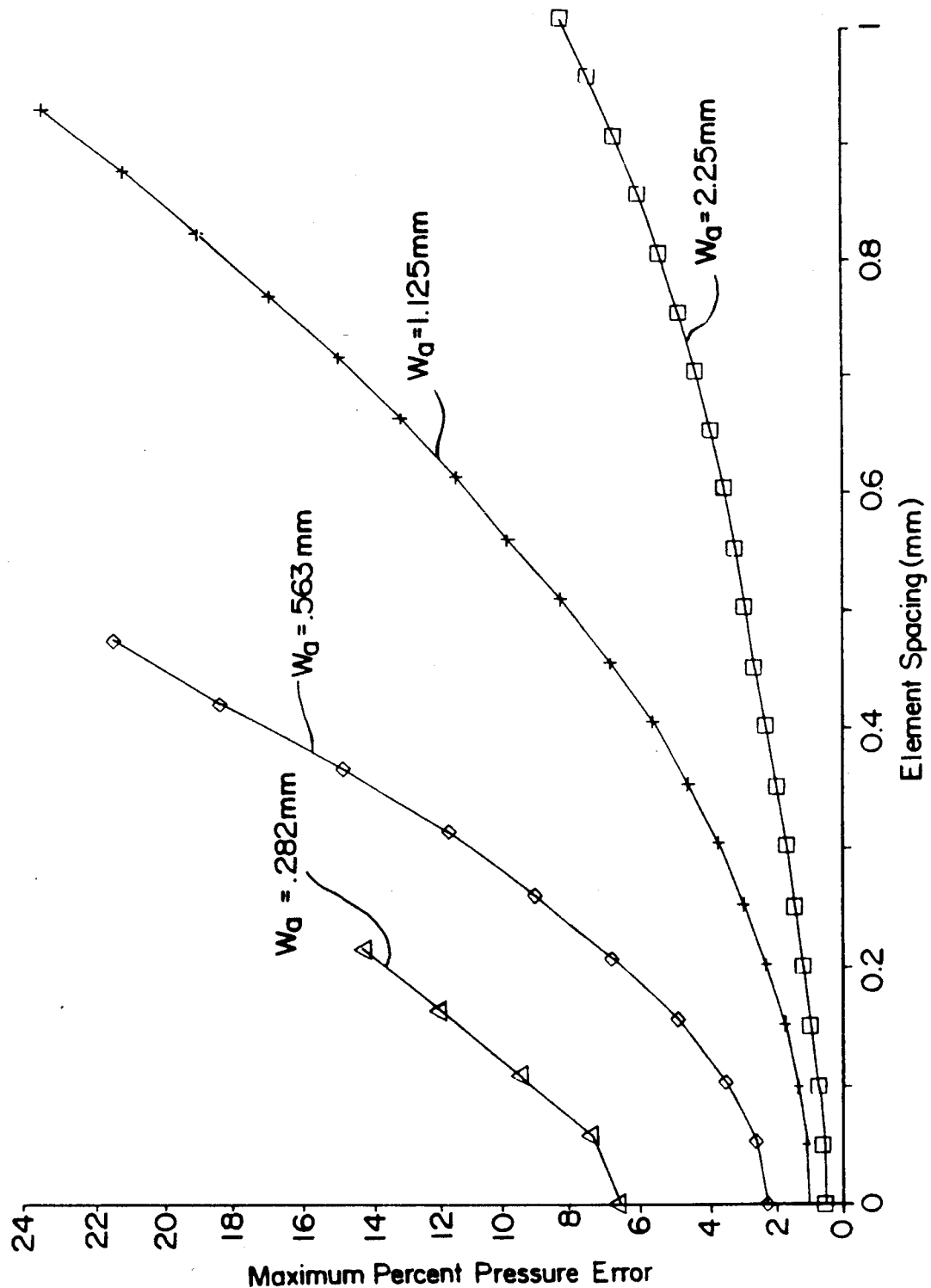
FIG. 13 shows plots of maximum percent pressure error versus sensor element spacing in accordance with the error correction method and mathematical models of the present invention.

In the preferred embodiment, the inaccuracies due to element spacing are also taken into account in the crosstalk error correction factor, e. FIG. 13 shows the effect of both crosstalk and element spacing on the accuracy of the blood pressure measurement based on the analytical model. Specifically, FIG. 13 shows in greater detail the calculated maximum pressure error for each of the several different apparent artery widths shown in FIG. 11. From FIG. 13, it is apparent that should an element 110 of the tonometer sensor be located precisely at the minimum of the dip (this would always occur if the element spacing=0 mm), the percent error in the blood pressure reading would be attributable solely to the crosstalk error as determined at the minimum of the dip in FIG. 11. This error is shown in FIG. 12. However, because of the finite element spacing, the element 110 which is closest to the minimum of the dip may in fact be offset from the minimum of the dip (when element spacing>0 mm) by as much as one-half the element spacing. Thus, the maximum measurement error plotted in FIG. 13 would occur when the strain gage is located at one half of the spacing interval from the minimum of the dip. This maximum error increases at a rate corresponding to the shape of the strain response to the applied artery pressure profile as shown in FIG. 11. FIG. 13 therefore graphically displays the measurement error due to both crosstalk and element spacing.

In the preferred embodiment of the present invention, the crosstalk error correction factor look-up table accordingly accounts for both the error due to crosstalk and the error due to element spacing by including the percent error attributable both to crosstalk and to element spacing. Therefore, as part of the preparation of software for the tonometer instrument, the calculations leading to FIGS. 12 and 13 must be repeated for several typical values of $W_a$ and D. As an example, consider the results of FIG. 13. If the element spacing of the tonometer sensor were 0.4 mm, the measurement error (from FIG. 13) for $W_a=0.563$ mm would range from about 2.3% to 18.5%, depending on where the sensor elements 110 happened to be relative to the center of the artery beneath the tonometer sensor 100. It could be argued that the "average" distance between a sensor element 110 and the center of the artery 120 will be 0.1 mm. This 0.1 mm distance corresponds to the maximum error that would occur with an element spacing of 0.2 mm. Therefore, the average expected error for 0.4 mm element spacing corresponds to 0.2 mm on the abscissa of FIG. 13. The corresponding error is about 7% (for $W_a=0.563$ mm) according to FIG. 13. Thus, for a tonometer sensor 100 with 0.4 mm gage spacing, $W_a=0.563$ mm, and D=32mm Hg, the average error due to crosstalk and element placement (or spacing) is 7%.

As an example, FIG. 4 shows part of a crosstalk error look-up table containing computed crosstalk (and element spacing) error correction factor, e, values for various values of $W_a$ and D. The 7% value discussed above is entered in the appropriate location in this table. The other entries of the FIG. 4 table are estimates, and were not computed exactly. However, a skilled artisan could follow the method described above to generate a suitable table for any desired values of element spacing, $W_a$, and D. The values so computed would be included in the software of a tonometer instrument employing the invention.

The present invention comprises a method of correcting the tonometric blood pressure measurement to minimize (or cancel) the errors shown in FIGS. 12 and 13. As previously described, these errors are caused by crosstalk inherent in the tonometer sensor, and by the finite spacing between adjacent elements of the tonometer sensor.

The methods and means described above use an analytical model to calculate the behavior of the sensor diaphragm when subjected to a typical artery pressure profile. This model is convenient and accurate. However, this model assumes that the diaphragm edges are supported rigidly, which is only approximately true. Increased accuracy may be obtained by using finite-element models to calculate sensor behavior. Finite-element modeling methods are well-known, and several systems and software packages are currently available that may be used to create and analyze a finite-element model of the sensor. Examples of these include:
Supertab from System Dynamics Research Corp.
Aries Concept Station from Aries Technology Inc.
ANSYS from Swanson Analysis Systems, Inc.

Figure 6C:
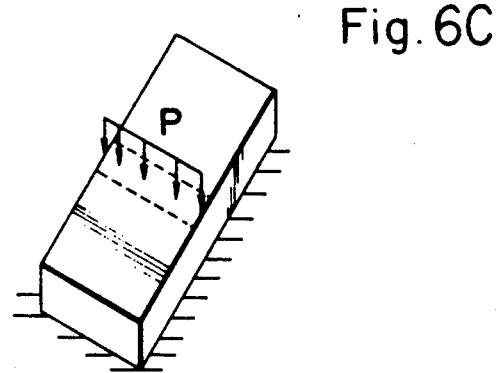

As an illustration of the use of finite-element modeling, the Aries Concept Station system was used to generate a finite-element model of a sensor with dimensions as shown in FIG. 6. Results of the computation for a pressure strip of half-width, u=0.2 mm, are shown in FIG. 9 and are denoted "FEM, U=0.2 mm." Note that the shape of the finite-element curve is different from the other, analytical model curves shown in FIG. 9 and more accurately represents the actual sensor behavior.

The process of computing the FIG. 4 table of correction factors may be performed exactly as described above by using the finite-element model calculations in place of analytical calculations. This process yields a table of correction factors similar to the FIG. 4 table. This new table will usually contain correction factors somewhat larger than those of FIG. 4.

Another embodiment of the invention described above includes fitting a polynomial function (for example a 4th or higher order polynomial with constant coefficients) to the measured spatial pressure distribution at some point after Point Q in the FIG. 5A algorithm. This would tend to make the algorithm more resistant to noise and inaccuracy of sensor pressure measurements.

Other modifications and variations to the invention will be apparent to those skilled in the art from the foregoing disclosure and teachings. It is therefore to be understood that, within the scope of the appended claims, the invention may be practiced otherwise than as specifically described. Thus, while only certain embodiments of the invention have been specifically described herein, it will be apparent that numerous modifications may be made thereto without departing from the spirit and scope of the invention.

What is claimed is:

1. A method for compensating for crosstalk behavior and element spacing of the sensor of an arterial tonometer instrument, which sensor has a plurality of pressure sensing elements disposed on at least one diaphragm, the method comprising the steps of:
   determining a measured artery pressure profile of a superficial artery;
   using at least one characteristic of said measured artery pressure profile to determine an error correction factor;
   determining an uncorrected blood pressure value; and
   calculating a corrected blood pressure value by applying said error correction factor to said uncorrected blood pressure value.

2. The method of claim 1, wherein said step of determining an uncorrected blood pressure value comprises the step of determining an uncorrected diastolic pressure value.

3. The method of claim 1, wherein said step of determining an uncorrected blood pressure value comprises the step of determining an uncorrected systolic pressure value.

4. The method of claim 1, further comprising the step of sampling an entire blood pressure waveform and correcting each sampled value by applying said error correction factor.

5. The method of claim 1, wherein said at least one characteristic comprises artery width $W_a$.

6. The method of claim 1, wherein said at least one characteristic comprises dip depth D.

7. The method of claim 6, wherein said at least one characteristic further comprises artery width $W_a$.

8. A method for compensating for crosstalk behavior and element spacing of the sensor of an arterial tonometer instrument, which sensor has a plurality of pressure sensing elements disposed on at least one diaphragm, the method comprising the steps of:
   determining a measured artery pressure profile of a superficial artery;
   using at least one characteristic of said measured artery pressure profile to retrieve an error correction factor from a precomputed error correction factor look-up table;
   determining an uncorrected blood pressure value; and
   calculating a corrected blood pressure value by applying said error correction factor to said uncorrected blood pressure value.

9. The method of claim 1, wherein said error correction factor look-up table is precomputed by a method comprising the steps of:
   analytically modeling said diaphragm;

using the results of said analytical modeling to obtain responses of said diaphragm to typical artery pressure profiles measured by a tonometer sensor placed over a superficial artery;

using said diaphragm responses to estimate errors in blood pressure measurements for said typical artery pressure profiles; and calculating error correction factors necessary to compensate for said errors, and indexing them in said error correction factor look-up table according to said at least one characteristic.

10. The method of claim 8, wherein said error correction factor look-up table is precomputed by a method comprising the steps of:

modeling said diaphragm using finite element methods;

using the results of said finite element modeling to obtain responses of said diaphragm to typical artery pressure profiles measured by a tonometer sensor placed over a superficial artery;

using said diaphragm responses to estimate errors in blood pressure measurements for said typical artery pressure profiles; and calculating error correction factors necessary to compensate for said errors, and indexing them in said error correction factor look-up table according to said at least one characteristic.

11. A method for compensating for crosstalk behavior and element spacing of the sensor of an arterial tonometer instrument, which sensor has a plurality of pressure sensing elements disposed on at least one diaphragm, the method comprising the steps of:

determining an apparent artery width $W_a$ of a subject artery;

determining a dip depth D for said artery;

using said apparent artery width $W_a$ and dip depth D to determine an error correction factor;

determining an uncorrected blood pressure value; and calculating a corrected blood pressure value by applying said error correction factor to said uncorrected blood pressure value.

12. The method of claim 11, wherein said step of determining said apparent artery width Wa comprises the steps of:

locating left and right local maximums of pressure; and calculating said apparent artery width $W_a$ as the distance between the locations of said left and right local maximums of pressure.

13. The method of claim 11, wherein said step of determining said dip depth D comprises the steps of:

locating a spatial local minimum of pressure;

locating left and right local maximums of pressure; and calculating said dip depth D as the average of respective differences between said left and right local maximums of pressure and said spatial local minimum of pressure.

14. The method of claim 11, wherein said apparent artery width $W_a$ and dip depth D are utilized to retrieve said error correction factor from a precomputed error correction factor look-up table.

15. The method of claim 14, wherein said error correction factor look-up table is precomputed by a method comprising the steps of:

analytically modeling said diaphragm;

using the results of said analytical modeling to obtain responses of said diaphragm to typical artery pressure profiles measured by a tonometer sensor placed over a superficial artery;

using said responses to estimate errors in blood pressure measurements for said typical artery pressure profiles; and calculating error correction factors necessary to compensate for said errors, and indexing them in said error correction factor look-up table according to said apparent artery width $W_a$ and dip depth D.

16. The method of claim 15, wherein said diaphragm is analytically modeled as a plate, rigidly-clamped at four edges, of predetermined length and width which is subjected to a strip of pressure of predetermined width and magnitude that is symmetrically oriented about the minor axis of said plate, and said typical artery pressure profiles are modeled by the superposition of several pressure strips.

17. The method of claim 14, wherein said error correction factor look-up table is precomputed by a method comprising the steps of:

modeling said sensor using finite element methods;

using the results of said finite element modeling to obtain responses of said sensor to typical artery pressure profiles measured by a tonometer sensor placed over a superficial artery;

using said responses to estimate errors in blood pressure measurements for said typical artery pressure profiles; and calculating error correction factors necessary to compensate for said errors, and indexing them in said error correction factor look-up table according to said apparent artery width $W_a$ and dip depth D.

18. A method for compensating for crosstalk behavior and element spacing of the sensor of an arterial tonometer instrument, which sensor has a plurality of pressure sensing elements disposed on at least one diaphragm, the method comprising the steps of:

locating a sensing element that measures a maximum pulse amplitude corresponding to blood pressure pulses in a subject artery;

locating a spatial local minimum of pressures measured by said sensing elements near to the sensing element measuring said maximum pulse amplitude;

locating left and right spatial local maximums of the pressures measured by the sensing elements which are indicative of the left and right edges, respectively, of said artery;

calculating a dip depth D as the average of respective differences between said left and right local maximums of pressure and said spatial local minimum of pressure;

calculating an apparent artery width $W_a$ as the distance between the locations of said left and right local maximums of pressure;

using said calculated dip depth D and apparent artery width Wa to retrieve an error correction factor from a precomputed error correction factor look-up table;

determining an uncorrected blood pressure value; and calculating a corrected blood pressure value by applying said error correction factor to said uncorrected blood pressure value.

19. The method of claim 18, wherein said error correction factor look-up table is precomputed by analytically modeling said tonometer sensor diaphragm.

20. The method of claim 18, wherein said error correction factor look-up table is precomputed using finite element modeling techniques on said tonometer sensor.

21. The method of claim 18 further comprising the step of sampling an entire blood pressure waveform and correcting each sampled value by applying said error correction factor.

22. The method of claim 18, wherein said left and right spatial local maximums of pressure are located within a predetermined distance from said spatial local minimum of pressure.

23. The method of claim 22, wherein said left and right spatial local maximums of pressure are located within about 0.4 mm to 1.5 mm of said spatial local minimum of pressure for adult subjects.

24. The method of claim 23, wherein said about 0.4 mm to 1.5 mm distance is replaced with lower values when a subject is smaller than a typical adult.

25. A method for compensating for crosstalk behavior and element spacing of the sensor of an arterial tonometer instrument, which sensor has a plurality of pressure sensing elements disposed on at least one diaphragm, the method comprising the steps of:
locating a sensing element that measures a maximum pulse amplitude corresponding to blood pressure pulses in a subject artery;
locating a spatial local minimum of pressures measured by the sensing elements near to the sensing element measuring said maximum pulse amplitude;
identifying left and right locations on said at least one diaphragm at which a measured pulse amplitude is a predetermined fraction of said maximum pulse amplitude and which lie right and left, respectively, of said sensing element measuring said maximum pulse amplitude, said left and right locations being indicative of the left and right edges, respectively, of said artery;
calculating a dip depth D as the average of respective differences between the pressures at said left and right locations and said spatial local minimum of pressure;
calculating an apparent artery width $W_a$ as the distance between said left and right locations;
using said calculated dip depth D and apparent artery width $W_a$ to retrieve an error correction factor from a precomputed error correction factor look-up table;
determining an uncorrected blood pressure value; and
calculating a corrected blood pressure value by applying said error correction factor to said uncorrected blood pressure value.

26. The method of claim 25, wherein said predetermined fraction is about 60 to about 90 percent.

27. An apparatus for externally measuring blood pressure in an artery, said apparatus comprising:
arterial tonometer instrument means, including a sensor having a plurality of pressure sensing elements disposed on at least one diaphragm, for determining an uncorrected blood pressure value;
means for determining a measured artery pressure profile of said artery;
means for using at least one characteristic of said measured artery pressure profile to determine an error correction factor; and
means for calculating a corrected blood pressure value by applying said error correction factor to said uncorrected blood pressure value.

28. An apparatus for externally measuring blood pressure in an artery, said apparatus comprising:
arterial tonometer instrument means, including a sensor having a plurality of pressure sensing elements disposed on at least one diaphragm, for determining an uncorrected blood pressure value;
means for determining an apparent artery width $W_a$ of said artery;
means for determining a dip depth D for said artery;
means for using said apparent artery width $W_a$ and dip depth D to determine an error correction factor; and
means for calculating a corrected blood pressure value by applying said error correction factor to said uncorrected blood pressure value.

29. An arterial tonometer instrument, including a sensor having a plurality of pressure sensing elements disposed on at least one diaphragm, for externally measuring blood pressure in an artery, comprising:
means for locating a sensing element that measures a maximum pulse amplitude corresponding to blood pressure pulses in said artery;
means for locating a spatial local minimum of pressure measured by the plurality of pressure sensing elements near to the sensing element measuring said maximum pulse amplitude;
means for locating left and right local maximums of pressure measured by the sensing elements which are indicative of the left and right edges, respectively, of said artery;
means for determining an uncorrected blood pressure value;
means for calculating a dip depth D as the average of respective differences between said left and right local maximums of pressure and said spatial local minimum of pressure;
means for calculating an apparent artery width $W_a$ as the distance between the locations of said left and right local maximums of pressure;
means for using said calculated dip depth D and apparent artery width $W_a$ to retrieve an error correction factor from a precomputed error correction factor look-up table; and
means for calculating a corrected blood pressure value by applying said error correction factor to said uncorrected blood pressure value.

30. An arterial tonometer instrument, including a sensor having a plurality of pressure sensing elements disposed on at least one diaphragm, for externally measuring blood pressure in an artery, comprising:
means for locating a sensing element that measures a maximum pulse amplitude corresponding to blood pressure pulses in said artery;
means for locating a spatial local minimum of pressure measured by said plurality of pressure sensing elements near to the sensing element measuring said maximum pulse amplitude;
means for identifying left and right locations on said at least one diaphragm at which a measured pulse amplitude is a predetermined fraction of said maximum pulse amplitude, said left and right locations being indicative of the left and right edges, respectively, of said artery;
means for determining an uncorrected blood pressure value;
means for calculating a dip depth D as the average of respective differences between measured pressures at said left and right locations and said spatial local minimum of pressure;

means for calculating an apparent artery width $W_a$ as the distance between said left and right locations;

means for using said calculated dip depth D and apparent artery width $W_a$ to retrieve an error correction factor from a precomputed error look-up table; and means for calculating a corrected blood pressure value by applying said error correction factor to said uncorrected blood pressure value.

31. A method for constructing an error correction factor look-up table for use in compensating for crosstalk behavior and element spacing of the sensor of an arterial tonometer instrument, which sensor has a plurality of sensing elements disposed on at least one diaphragm, the method comprising the steps of:

modeling at least one of said sensor and said diaphragm;

using the results of said modeling to obtain responses of at least one of said sensor and said diaphragm to typical artery pressure profiles measured by a tonometer sensor placed over a superficial artery;

using said responses to estimate errors in blood pressure measurements for said typical artery pressure profiles; and calculating error correction factors necessary to compensate for said errors.

32. The method of claim 31, wherein said typical artery pressure profiles are characterized by two parameters, apparent artery width Wa and dip depth D, and said error correction factors are indexed in said error correction factor look-up table according to said two parameters.

33. The method of claim 31, wherein said diaphragm is modeled using an analytical model.

34. The method of claim 33, wherein said analytical model of said diaphragm is a plate, rigidly-clamped at four edges, of predetermined length and width which is subjected to a strip of pressure of predetermined width and magnitude that is symmetrically oriented about the minor axis of said plate, and wherein said analytical model of said diaphragm is used to obtain, by superposition of the solutions for several strips of pressure of varying widths and magnitudes, said responses to said typical artery pressure profiles.

35. The method of claim 31, wherein said sensor and diaphragm are modeled using finite element methods.

36. A method for constructing an error correction factor look-up table for use in compensating for crosstalk behavior and element spacing of the sensor of an arterial tonometer instrument, which sensor has a plurality of sensing elements disposed on at least one diaphragm, the method comprising the steps of:

analytically modeling said diaphragm as a plate, rigidly-clamped at four edges, of predetermined length and width which is subjected to a strip of pressure of predetermined width and magnitude that is symmetrically oriented about the minor axis of said plate;

using the results of said analytical modeling to obtain, by superposition of solutions for several strips of pressure of varying widths and magnitudes, responses of said diaphragm to typical artery pressure profiles measured by a tonometer sensor placed over a superficial artery;

using said responses to estimate errors in blood pressure measurements for said typical artery pressure profiles; and calculating error correction factors necessary to compensate for said errors.

37. The method of claim 36, wherein said typical artery pressure profiles are characterized by two parameters, apparent artery width $W_a$ and dip depth D, and said error correction factors are indexed in said error correction factor look-up table according to said two parameters.

* * * * *